United States Patent
Li

(10) Patent No.: US 7,351,858 B2
(45) Date of Patent: Apr. 1, 2008

(54) ORTHO-SUBSTITUTED BENZOIC ACID DERIVATIVES FOR THE TREATMENT OF INSULIN RESISTANCE

(75) Inventor: Lanna Li, Molndal (SE)

(73) Assignee: AstraZeneca AB, Sodertalje (SE)

( * ) Notice: Subject to any disclaimer, the term of this patent is extended or adjusted under 35 U.S.C. 154(b) by 437 days.

(21) Appl. No.: 10/519,376

(22) PCT Filed: Jun. 17, 2003

(86) PCT No.: PCT/GB03/02591

§ 371 (c)(1),
(2), (4) Date: Dec. 20, 2004

(87) PCT Pub. No.: WO04/000294

PCT Pub. Date: Dec. 31, 2003

(65) Prior Publication Data

US 2005/0222261 A1    Oct. 6, 2005

(30) Foreign Application Priority Data

Jun. 20, 2002 (SE) .................................... 0201936

(51) Int. Cl.
*C07C 229/00* (2006.01)
*A61K 31/195* (2006.01)

(52) U.S. Cl. ...................... 562/450; 514/563

(58) Field of Classification Search ................ 514/563; 562/450

See application file for complete search history.

(56) References Cited

U.S. PATENT DOCUMENTS

| 5,750,783 A | 5/1998 | Goldmann et al. |
| 6,258,850 B1 | 7/2001 | Andersson |
| 2002/0022656 A1 | 2/2002 | Saurberg et al. |

FOREIGN PATENT DOCUMENTS

| EP | 802 186 | 10/1997 |
| EP | 1 184 366 | 3/2002 |
| WO | WO-99/32477 | 7/1999 |
| WO | WO-00/64876 | 11/2000 |
| WO | WO-00/64888 | 11/2000 |
| WO | WO-2004/000295 | 12/2003 |

*Primary Examiner*—Taylor Victor Oh
(74) *Attorney, Agent, or Firm*—Pepper Hamilton LLP

(57) ABSTRACT

The present invention provides a compound of formula (I), wherein n is 0, 1 or 2; $R^1$ represents halo, a $C_{1-4}$alkyl group which is optionally substituted by one or more fluoro, a $C_{1-4}$alkoxy group which is optionally substituted by one or more fluoro and wherein when n is 2 the substituents $R^1$ may be the same or different; $R^2$ represents an unbranched $C_{2-7}$alkyl group; $R^3$ represents H or $OCH_3$; and W represents O or S and pharmaceutically acceptable salts and prodrugs thereof, to processes for preparing such compounds, to their utility in treating clinical conditions associated with insulin resistance, to methods for their therapeutic use and to pharmaceutical compositions containing them.

7 Claims, No Drawings

ORTHO-SUBSTITUTED BENZOIC ACID DERIVATIVES FOR THE TREATMENT OF INSULIN RESISTANCE

This application is a national stage filing under 35 U.S.C. 371 of PCT application PCT/GB2003/002591 filed Jun. 17, 2003, which claims priority from Sweden Application No. 0201936-2, filed Jun. 20, 2002, the specifications of each of which are incorporated by reference herein.

FIELD OF THE INVENTION

The present invention relates to certain novel benzoic acid derivatives, to processes for preparing such compounds, to their utility in treating clinical conditions associated with insulin resistance, to methods for their therapeutic use and to pharmaceutical compositions containing them.

BACKGROUND OF THE INVENTION

The Insulin Resistance Syndrome (IRS) including type 2 diabetes mellitus, which refers to a cluster of manifestations including insulin resistance with accompanying hyperinsulnaemia, possible type 2 diabetes mellitus, arterial hypertension, central (visceral) obesity, dyslipidaemia observed as deranged lipoprotein levels typically characterised by elevated VLDL (very low density lipoproteins), small dense LDL particles and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus atherosclerosis related conditions cause up to 80% of all deaths.

In clinical medicine there is awareness of the need to increase the insulin sensitivity in IRS suffering patients and thus to correct the dyslipidaemia which is considered to cause the accelerated progress of atherosclerosis. However, currently this is not a universally well defined disease.

The S-enantiomer of the compound of formula C below

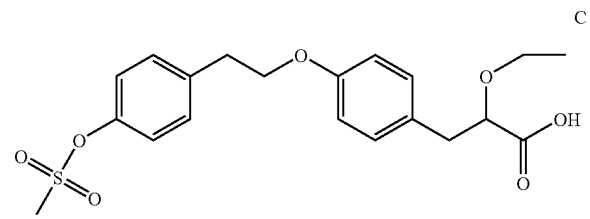

C 2-ethoxy-3-[4-(2-{4-methanesulfonyloxyphenyl}ethoxy)phenyl]propanoic acid, is disclosed in PCT Publication Number WO99/62872. This compound is reported to be a modulator of peroxisome proliferator-activated receptors (PPAR, for a review of the PPARs see T. M. Willson et al, J Med Chem 2000, Vol 43, 527) and has combined PPARα/PPARγ agonist activity (Structure, 2001, Vol 9, 699, P. Cronet et al). This compound is effective in treating conditions associated with insulin resistance.

Surprisingly a series of compounds has now been found which are selective PPARα modulators.

DESCRIPTION OF THE INVENTION

The present invention provides a compound of formula I

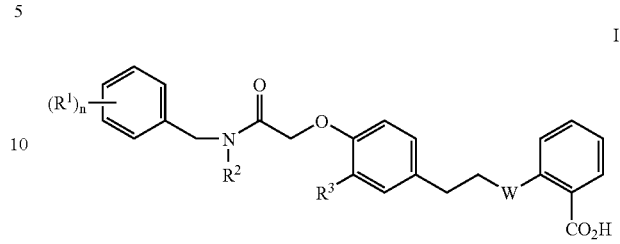

I wherein n is 0, 1 or 2;
$R^1$ represents halo, a $C_{1-4}$alkyl group which is optionally substituted by one or more fluoro, a $C_{1-4}$alkoxy group which is optionally substituted by one or more fluoro and wherein when n is 2 the substituents $R^1$ may be the same or different;
$R^2$ represents an unbranched $C_{2-7}$alkyl group;
$R^3$ represents H or $OCH_3$; and
W represents O or S and pharmaceutically acceptable salts and prodrugs thereof.

Further values of $R^1$, $R^2$, $R^3$ and W in compounds of Formula I now follow. It will be understood that such values may be used with any of the definitions, claims or embodiments defined hereinbefore or hereinafter.

In a first aspect $R^1$ is halo, a $C_{1-4}$alkyl group or a $C_{1-4}$alkoxy group and n is 0, 1 or 2. Particularly $R^1$ is fluoro, chloro or trifluoromethyl when n is 1. Particularly $R^1$ is fluoro when n is 2.

In a second aspect $R^2$ represents ethyl or hexyl.
In a third aspect $R^3$ represents H.
In a fourth aspect $R^3$ represents OMe.
In a fifth aspect W represents O.
In a sixth aspect W represents S.

The term unbranched $C_{2-7}$alkyl denotes a straight-chain, saturated aliphatic hydrocarbon having from 2 to 7 carbon atoms. Examples of said alkyl include ethyl, n-propyl, n-butyl n-pentyl, n-hexyl and n-heptyl.

It will be understood by those skilled in the art that the term interrupted as used above means that the oxygen atom is situated within the alkyl chain and is not the terminal atom. The term "prodrug" as used in this specification includes derivatives of the carboxylic acid group which are converted in a mammal, particularly a human, into the carboxylic acid group or a salt or conjugate thereof. It should be understood that, whilst not being bound by theory, it is believed that most of the activity associated with the prodrugs arises from the activity of the compound of formula I into which the prodrugs are converted. Prodrugs can be prepared by routine methodology well within the capabilities of someone skilled in the art. Various prodrugs of carboxy are known in the art. For examples of such prodrug derivatives, see:

a) Design of Prodrugs, edited by H. Bundgaard, (Elsevier, 1985) and Methods in Enzymology. 42: 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8:1-38 (1992);

d) H. Bundgaard, et al., Journal of Pharmaceutical Sciences, 77:285 (1988); and
e) N. Kakeya, et al., Chem Pharm Bull, 32:692 (1984).

The above documents a to e are herein incorporated by reference.

In vivo cleavable esters are just one type of prodrug of the parent molecule.

The compounds of formula I have activity as medicaments, in particular the compounds of formula I are selective agonists of PPARα, that is, their $EC_{50}$ for PPARα is at least four times lower and preferably at least 10 or 50 times lower than their respective $EC_{50}$ for PPARγ wherein the $EC_{50}$s are measured and calculated as described in the assays later in this document. The compounds of formula I are potent and selective.

The present invention provides a compound selected from:

2-[2-(4-{2-[ethyl(2-fluorobenzyl)amino]-2-oxoethoxy}phenyl)ethoxy]benzoic acid;

2-[2-(4-{2-[(2,4-difluorobenzyl)(heptyl)amino]-2-oxoethoxy}-3-methoxyphenyl)-ethoxy]benzoic acid;

2-[2-(4-{2-[(4-chlorobenzyl)(ethyl)amino]-2-oxoethoxy}phenyl)ethylthio]benzoic acid;

2-[2-(4-{2-[(4-chlorobenzyl)(ethyl)amino]-2-oxoethoxy}phenyl)ethoxy]benzoic acid;

2-[2-(4-{2-[ethyl(4-trifluoromethylbenzyl)amino]-2-oxoethoxy}phenyl)ethoxy]benzoic acid;

2-[2-(4-{2-[ethyl(4-trifluoromethylbenzyl)amino]-2-oxoethoxy}phenyl)ethylthio]benzoic acid;

2-{2-[4-(2-{butyl[2-fluoro-4-(trifuoromethyl)benzyl]amino}-2-oxoethoxy)phenyl]-ethoxy}benzoic acid;

2-[2-(4-{2-[(2,4-difluorobenzyl)(propyl)amino]-2-oxoethoxy}phenyl)ethoxy]benzoic acid;

2-[2-(4-{2-[benzyl(ethyl)amino]-2-oxoethoxy}phenyl)ethoxy]benzoic acid;

2-{[2-(4-{2-[benzyl(ethyl)amino]-2-oxoethoxy}phenyl)ethyl]thio}benzoic acid;

2-[2-(4-{2-[(4-tert-butylbenzyl)(ethyl)amino]-2-oxoethoxy}phenyl)ethoxy]benzoic acid;

2-[2-(4-{2-[ethyl(4-fluorobenzyl)amino]-2-oxoethoxy}phenyl)ethoxy]benzoic acid;

2-{[2-(4-{2-[ethyl(2-fluorobenzyl)amino]-2-oxoethoxy}phenyl)ethyl]thio}benzoic acid; or 2-{[2-(4-{2-[(2-chlorobenzyl)(ethyl)amino]-2-oxoethoxy}phenyl)ethyl]thio}benzoic acid and pharmaceutically acceptable salts thereof.

Particularly the compound is selected from:

2-[2-(4-{2-[ethyl(2-fluorobenzyl)amino]-2-oxoethoxy}phenyl)ethoxy]benzoic acid;

2-[2-(4-{2-[(4-chlorobenzyl)(ethyl)amino]-2-oxoethoxy}phenyl)ethylthio]benzoic acid;

2-[2-(4-{2-[(2,4-difluorobenzyl)(propyl)amino]-2-oxoethoxy}phenyl)ethoxy]benzoic acid;

2-[2-(4-{2-[benzyl(ethyl)amino]-2-oxoethoxy}phenyl)ethoxy]benzoic acid; or

2-[2-(4-{2-[ethyl(4-fluorobenzyl)amino]-2-oxoethoxy}phenyl)ethoxy]benzoic acid;

It will also be understood that certain compounds of the present invention may exist in solvated, as well as unsolvated forms. It is to be understood that the present invention encompasses all such solvated forms. Certain compounds of the present invention may exist as tautomers. It is to be understood that the present invention encompasses all such tautomers.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof. Isomers may be separated using conventional techniques, e.g. chromatography or fractional crystallisation. The enantiomers may be isolated by separation of racemate for example by fractional crystallisation, resolution or HPLC. The diastereomers may be isolated by separation of isomer mixtures for instance by fractional crystallisation, HPLC or flash chromatography. Alternatively the stereoisomers may be made by chiral synthesis from chiral starting materials under conditions which will not cause racemisation or epimerisation, or by derivatisation, with a chiral regent. All stereoisomers are included within the scope of the invention.

Methods of Preparation

The compounds of the invention may be prepared as outlined below. However, the invention is not limited to these methods, the compounds may also be prepared as described for structurally related compounds in the prior art. The reactions can be carried out according to standard procedures or as described in the experimental section.

Compounds of formula I may be prepared by reacting a compound of formula II

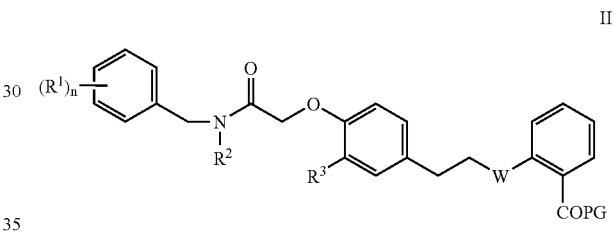

II in which $R^1$, $R^2$, $R^3$, W and n are as previously defined and PG represents a protecting group for a carboxylic hydroxy group as described in the standard text "Protective Groups in Organic Synthesis", $2^{nd}$ Edition (1991) by Greene and Wuts, with a de-protecting agent. The protecting group may also be a resin, such as Wang resin or 2-chlorotrityl chloride resin. Protecting groups may be removed in accordance to techniques which are well known to those skilled in the art. One such protecting group is where PG represents $C_{1-6}$alkoxy group or an arylalkoxy group eg benzyl, such that COPG represents an ester. Such esters can be reacted with a hydrolysing agent, for example lithium hydroxide in the presence of a solvent for example a mixture of THF and water or potassium hydroxide in a $C_{1-3}$ alcohol for example methanol, at a temperature in the range of 0-200° C. or by microwave radiation to give compounds of formula I.

Compounds of formula II may be prepared by reacting a compound of formula III

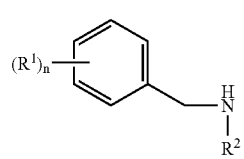

III or a salt thereof, for example a hydrochloride salt, in which $R^1$, $R^2$ and n are as previously defined with a compound of formula IV

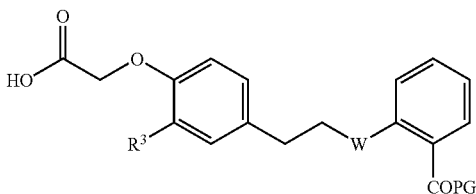

or the acid chloride thereof in which $R^3$, W and PG are as previously defined in an inert solvent, for example dichloromethane, optionally in the presence of a coupling agent, for example 4-dimethylaminopyridine or 1-ethyl-3-(3-dimethylaminopropyl)carbodiimide hydrochloride, at a temperature in the range of –25° C. to 150° C.

Compounds of formula II may also be prepared by reacting a compound of formula V

in which PG is as previously defined with a compound of formula VI

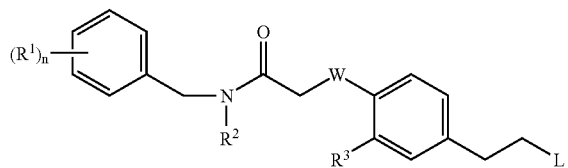

in which $R^1$, $R^2$, $R^3$, W and n are as previously defined and L represents a leaving group, for example methylsulphonyloxy or halo, e.g. bromo, optionally in the presence of solvent, for example acetonitrille, and optionally in the presence of a base, for example potassium carbonate, at a temperature in the range of 0 to 150° C.

Compounds of formula III, IV, V and VI may be prepared by methods described in the Examples or by analogous methods known to those skilled in the art.

Compounds of formula II, III, IV and V are useful intermediates in the preparation of compounds of formula I. Certain of these compounds are believed to be novel. Novel compounds of formula II, or formula m, or formula IV or formula V are herein claimed as a further aspect of the present invention.

The compounds of the invention may be isolated from their reaction mixtures using conventional techniques.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

In any of the preceding methods of preparation, where necessary, hydroxy, amino or other reactive groups may be protected using a protecting group, $R^p$ as described in the standard text "Protective groups in Organic Synthesis", $2^{nd}$ Edition (1991) by Greene and Wuts. The protecting group may also be a resin, such as Wang resin or 2-chlorotrityl chloride resin. The protection and deprotection of functional groups may take place before or after any of the reaction steps described hereinbefore. Protecting groups may be removed in accordance to techniques which are well known to those skilled in the art.

The expression "inert solvent" refers to a solvent which does not react with the starting materials, reagents, intermediates or products in a manner which adversely affects the yield of the desired product.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient either as a free acid, or a pharmaceutically acceptable salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001-100 mg/kg body weight, preferably 0.001-10 mg/kg body weight.

Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable salt thereof, in admixture with pharmaceutically acceptable adjuvants, diluents and/or carriers.

Pharmacological Properties

The present compounds of formula (I) are useful for the prophylaxis and/or treatment of clinical conditions associated with inherent or induced reduced sensitivity to insulin (insulin resistance) and associated metabolic disorders (also known as metabolic syndrome). These clinical conditions will include, but will not be limited to, general obesity, abdominal obesity, arterial hypertension, hyperinsulinaemia, hyperglycaemia, type 2 diabetes and the dyslipidaemia characteristically appearing with insulin resistance. This dyslipidaemia, also known as the atherogenic lipoprotein profile, is characterised by moderately elevated non-esterified fatty acids, elevated very low density lipoprotein (VLDL) triglyceride rich particles, high Apo B levels, low high density lipoprotein (HDL) levels associated with low apoAI particle levels and high Apo B levels in the presence of small, dense, low density lipoproteins (LDL) particles, phenotype B.

The compounds of the present invention are expected to be useful in treating patients with combined or mixed hyperlipidemias or various degrees of hypertriglyceridemias and postprandial dyslipidemia with or without other manifestations of the metabolic syndrome.

Treatment with the present compounds is expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency of the lower extremities. Because of their insulin sensitizing effect the compounds of formula I are also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed. Furthermore the compounds may be useful in treatment of various conditions outside the cardiovascular system whether or not associated with insulin resistance, like polycystic ovarian syndrome, obesity, cancer and states of inflammatory disease including neurodegenerative disorders such as mild cognitive impairment, Alzheimer's disease, Parkinson's disease and multiple sclerosis.

The compounds of the present invention are expected to be useful in controlling glucose levels in patients suffering from type 2 diabetes.

The present invention provides a method of treating or preventing dyslipidemias, the insulin resistance syndrome and/or metabolic disorders (as defined above) comprising the administration of a compound of formula I to a mammal (particularly a human) in need thereof.

The present invention provides a method of treating or preventing type 2 diabetes comprising the administration of an effective amount of a compound of formula I to a mammal (particularly a human) in need thereof.

In a further aspect the present invention provides the use of a compound of formula I as a medicament.

In a further aspect the present invention provides the use of a compound of formula I in the manufacture of a medicament for the treatment of insulin resistance and/or metabolic disorders.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes and obesity. The compounds of the invention may be combined with another therapeutic agent that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula I, or a pharmaceutically acceptable salt, solvate, solvate of such a salt or a prodrug thereof, may be administered in association with another PPAR modulating agent. PPAR modulating agents include but are not limited to a PPAR alpha and/or gamma and/or delta agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to BMS 298585, clofibrate, fenofibrate, bezafibrate, gemfibrozil and ciprofibrate; GW 9578, pioglitazone, rosiglitazone, rivoglitazone, balaglitazone, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxy-phenyl}ethoxy)phenyl]propanoic acid and pharmaceutically acceptable salts thereof.

In addition the combination of the invention may be used in conjunction with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin selected from the group consisting of atorvastatin, bervastatin, cerivastatin, dalvastatin, fluvastatin, itavastatin, lovastatin, mevastatin, nicostatin, nivastatin, pravastatin and siruvastatin, or a pharmaceutically acceptable salt, especially sodium or calcium, or a solvate thereof, or a solvate of such a salt. A particular statin is atorvastatin, or a pharmaceutically acceptable salt, solvate, solvate of such a salt or a prodrug thereof. A more particular statin is atorvastatin calcium salt. A particularly preferred statin is, however, a compound with the chemical name (E)-7-[4-(4-fluorophenyl)-6-isopropyl-2-[methyl(methylsulfonyl)-amino]-pyrimidin-5-yl](3R,5S)-3,5-dihydroxyhept-6-enoic acid, [also known as (E)-7-[4-(4-fluorophenyl)-6-isopropyl-2-[N-methyl-N-(methylsulfonyl)-amino]pyrimidin-5-yl] (3R,5S)-3,5-dihydroxyhept-6-enoic acid] or a pharmaceutically acceptable salt or solvate thereof, or a solvate of such a salt. The compound (E)-7-[4-(4-fluorophenyl)-6-isopropyl-2-[methyl-(methylsulfonyl)-amino]-pyrimidin-5-yl] (3R,5S)-3,5-dihydroxyhept-6-enoic acid, and its calcium and sodium salts are disclosed in European Patent Application, Publication No. EP-A-0521471, and in Bioorganic and Medicinal Chemistry, (1997), 5(2), 437-444. This latter statin is now known under its generic name rosuvastatin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with a bile acid sequestering agent, for example colestipol or cholestyramine or cholestagel.

The present invention also includes a compound of the present invention in combination with an inhibitor of the ileal bile acid transport system (IBAT inhibitor).

Suitable compounds possessing IBAT inhibitory activity have been described, see for instance the compounds described in WO 93/16055, WO 94/18183, WO 94/18184, WO 94/24087, WO 96/05188, WO 96/08484, WO 96/16051, WO 97/33882, WO98/07749, WO 98/38182, WO 98/40375, WO 98/56757, WO 99/32478, WO 99/35135, WO 99/64409, WO 99/64410, WO 00/01687, WO 00/20392, WO 00/20393, WO 00/20410, WO 00/20437, WO 01/34570, WO 00/35889, WO 00/47568, WO 00/61568, WO 01/68637, WO 01/68096, WO 02/08211, WO 00/38725, WO 00/38726, WO 00/38727, WO 00/38728, WO 00/38729, DE 19825804, JP 10072371, U.S. Pat. No. 5,070,103, EP 251 315, EP 417 725, EP 489 423, EP 549 967, EP 573 848, EP 624 593, EP 624 594, EP 624 595, EP 869 121, EP 864 582, and EP 1 070 703, and the contents of these patent applications, particularly the compounds described in claim 1 and the named examples, are incorporated herein by reference.

Particular classes of IBAT inhibitors suitable for use in the present invention are benzothiepines, and the compounds described in the claims, particularly claim 1, of WO 00/01687, WO 96/08484 and WO 97/33882 are incorporated herein by reference. Other suitable classes of IBAT inhibitors are the 1,2-benzomitiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). Other suitable IBAT inhibitors include one of:

1,1-dioxo-3,3-dibutyl-5-phenyl-7-methylthio-8-(N-{(R)-1'-phenyl-1'-[N'-(carboxymethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl] methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl] ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl] benzyl}carbamoylmethoxy)-2,3,4,5-tetrahydro-1,5-benzothiazepine;

1,1-dioxo-3,3-dibutyl-5-phenyl-7-methoxy-8-[N-{(R)-α [N'-(2-sulphoethyl)carbanoyl]-4-hydroxybenzyl}carbamylmethoxy]-2,3,4,5-tetrahydro-1,5-benzothiazepine;

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl)prop-2-yl]carbamoyl}-4-hydroxybenzyl)carbamoylmethoxy]-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbarmoyl]-4-hydroxybenzyl}carbamoylmethoxy)-2,3,4,5-tetrahydro-1,2,5-benzothiadiazepine; and 1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

According to an additional further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from:

a CETP (cholesteryl ester transfer protein) inhibitor, for example those referenced and described in WO 00/38725 page 7 line 22-page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751-54, 1998 which are incorporated herein by reference;

a nicotinic acid derivative, including slow release and combination products, for example, nicotinic acid (niacin), acipimox and niceritrol;

a phytosterol compound for example stanols;

probucol;

an anti-obesity compound for example orlistat (EP 129,748) and sibutramine (GB 2,184,122 and U.S. Pat. No. 4,929,629);

an omega-3 fatty acid for example Omacor™;

an antihypertensive compound for example an angiotensin converting enzyme (ACE) inhibitor, an angiotensin II receptor antagonist, an andrenergic blocker, an alpha andrenergic blocker, a beta andrenergic blocker for example metoprolol, a mixed alpha/beta andrenergic blocker, an andrenergic stimulant, calcium channel blocker, an AT-1 blocker, a saluretic, a diuretic or a vasodilator;

a CB1 antagonist or inverse agonist for example as described in WO01/70700 and EP 65635;

aspirin;

a Melanin concentrating hormone (MCH) antagonist;

a PDK inhibitor; or modulators of nuclear receptors for example LXR, FXR, RXR, and RORalpha;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula I include but are not limited to, the following compounds: alacepril, alatriopril, altiopril calcium, ancovenin, benazepril, benazepril hydrochloride, benazeprilat, benzoylcaptopril, captopril captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula I include, but are not limited to, compounds: candesartan, candesartan cilexetil, losartan, valsartan, irbesartan, tasosaran, telmisartan and eprosartan. Particularly preferred angiotensin II antagonists or pharmaceutically acceptable derivatives thereof for use in the present invention are candesartan and candesartan cilexetil.

Therefore in an additional feature of the invention, there is provided a method for for the treatment of type 2 diabetes and its associated complications in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt, solvate, solvate of such a salt or a prodrug thereof in simultaneous, sequential or separate administration with an effective amount of one the other compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt, solvate, solvate of such a salt or a prodrug thereof, and one of the other compounds described in this combination section or a pharmaceutically acceptable salt, solvate, solvate of such a salt or a prodrug thereof.

According to a further aspect of the present invention there is provided a kit comprising:
a) a compound of formula I, or a pharmaceutically acceptable salt, solvate, solvate of such a salt or a prodrug thereof, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to a further aspect of the present invention there is provided a kit comprising:
a) a compound of formula I, or a pharmaceutically acceptable salt, solvate, solvate of such a salt or a prodrug thereof, together with a pharmaceutically acceptable diluent or carrier, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the the treatment of metabolic syndrome or type 2 diabetes and its associated complications in a warm-blooded animal, such as man.

According to another feature of the invention there is provided the use of a compound of the formula I, or a pharmaceutically acceptable salt, solvate, solvate of such a salt or a prodrug thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt, solvate, solvate of such a salt or a prodrug thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

WORKING EXAMPLES $^1$H NMR and $^{13}$C NMR measurements were performed on a Varian Mercury 300 or Varian UNITY plus 400, 500 or 600 spectrometers, operating at $^1$H frequencies of 300, 400, 500 and 600 MHz, respectively, and at $^{13}$C frequencies of 75, 100, 125 and 150 MHz, respectively. Measurements were made on the delta scale (δ).

Unless otherwise stated, chemical shifts are given in ppm with the solvent as internal standard.

ABBREVIATIONS

| | |
|---|---|
| IRS | insulin resistance syndrome |
| TLC | thin layer chromatography |
| HOBT | 1-hydroxybenzotriazole-hydrate |
| DIBAH | diisobutylaluminium hydride |
| DMSO | dimethyl sulfoxide |
| EtOAc | ethyl acetate |
| DMF | N,N-dimethylformamide |
| THF | tetrahydrofuran |

-continued

| | |
|---|---|
| HPLC | high performance liquid chromatography |
| MeCN | acetonitrile |
| TFA | trifluoroacetic acid |
| Pd/C | palladium on charcoal |
| HATU | O-(7-azabenzotriazolyl-1-yl)-N,N,N',N'-tetramethyluronium hexafluorophosphate |
| DCM | dichloromethane |
| TBTU | O-(benzotriazol-1-yl)-N,N,N',N'-tetramethyluronium tetrafluoroborate |
| DIPEA | N,N-diisopropylethylamine |
| DMAP | 4-dimethylaminopyridine |
| Trisamine | Tris(hydroxymethyl)aminomethane |
| ISOLUTE ® FLASH Si | is a silica column suitable for chromatography Borohydride on polymer support is Borohydride on Amberlite IRA-400 available from Aldrich |
| LC-MS | liquid chromatography- mass spectroscopy |
| RT | room temperature |
| t | triplet |
| s | singlet |
| d | doublet |
| q | quartet |
| qvint | quintet |
| m | multiplet |
| br | broad |
| bs | broad singlet |
| dm | doublet of multiplet |
| bt | broad triplet |
| dd | doublet of doublets |

Example 1 a) Tert-butyl [4-(2-hydroxyethyl)phenoxy]acetate

A mixture of 4-(2-hydroxyethyl)phenol (3.8 ml, 25.834 mmol) was dissolved in acetonitrile (25 ml), potassium carbonate (7.085 g, 51.267 mmol) and tert-butyl bromoacetate (5.000 g, 25.834 mmol) was boiled under reflux for 16 hours. The solvent was evaporated under reduced pressure. The residue was dissolved in EtOAc and washed with brine and water, dried with $MgSO_4$ and evaporated under reduced pressure to give the desired product was obtained (6.00 g, yield 92.8%).

$^1$H-NMR (400 MHz, $CDCl_3$): 1.52 (s, 9H), 2.98 (t, 2H), 3.46 (t, 2H), 4.92 (s, 2H), 6.89-6.97 (m, 4H)

b) Tert-butyl (4-{2-[(methylsulfonyl)oxy]ethyl}phenoxy)acetate

Tert-butyl [4-(2-hydroxyethyl)phenoxy]acetate (6.000 g, 23.781 mmol) and triethylamine (9.9 ml, 71.341 mmol) were dissolved in DCM. The mixture was cooled to −10° C. and methanesulfonyl chloride (2.8 ml, 35.671 mmol) was added dropwise to the mixture. The reaction mixture was allowed to reach room temperature and was stirred for 16 hours. The mixture was diluted with DCM. The organic layer was washed with water, brine and 0.3M $KHSO_4$, dried with $MgSO_4$, and evaporated under reduced pressure. Obtained 7.5 g of light-yellow crystals (yield 95.5%).

$^1$H-NMR (400 MHz, $CDCl_3$): 1.52 (s, 9H), 2.98 (t, 2H),3.10(s, 3H), 3.46 (t, 2H), 4.92 (s, 2H), 6.89-6.97 (m, 4H)

c) Methyl 2-{2-[4-(2-tert-butoxy-2-oxoethoxy)phenyl]ethoxy}benzoate

Methyl salicylate (2.7 ml, 21.187 mmol) was dissolved in acetonitrile, and potassium carbonate (5.856 g, 42.373 mmol) was added. The mixture was cooled to −10° C. then tert-butyl (4-{2-[(methylsulfonyl)oxy]ethyl}phenoxy)acetate was added. The mixture was boiled under reflux for 16 hours, and then the solvent was evaporated under reduced pressure. The residue was dissolved in EtOAc, washed with water and brine, then the organic layer was dried with $MgSO_4$ and the solvent was removed by evaporation. The crude material was purified by flash chromatography (silica gel 60 0.004-0.063 mm) using EtOAc: Toluene 50:50 as the eluant. The fractions which contained the desired product were pooled, and solvent evaporated. This gave 5.0 g of pure product (yield 61.1%).

$^1$H-NMR (400 MHz, $CDCl_3$); 1.48 (s, 9H), 3.08 (s, 3H), 3.87 (t, 2H), 4.18 (t, 2H), 4.49 (s, 2H), 6.84 (d, 2H), 6.90-6.98 (m, 2H), 7.20-7.26 (m, 2H), 7.38-7.43 (m, 1H), 7.7 (dd, 1H)

d) (4-{2-[2-(methoxycarbonyl)phenoxy]ethyl}phenoxy)acetic acid

Methyl 2-{2-[4-(2-tert-butoxy-2-oxoethoxy)phenyl]ethoxy}benzoate (0.400 g, 1.0351 mmol) was dissolved in DCM and trifluoroacetic acid (0.8 ml, 8.281 mmol) was added. The mixture was stirred at room temperature for 3 h. The solvent was evaporated to give 325 mg of a white powder.

$^1$H-NMR (600 MHz, $CDCl_3$); 3.08 (t, 2H), 3.86 (s, 3H), 4.18 (t, 2H), 4.64 (s, 2H), 6.84-6.96 (m, 4H), 7,23 (d, 2H), 7.37-7.42 (m, 1H), 7.75 (dd, 1H)

e) Methyl 2-[2-(4-{2-[ethyl(2-fluorobenzyl)amino]-2-oxoethoxy}phenyl)ethoxy]-benzoate (4-{2-[2-(Methoxycarbonyl)phenoxy]ethyl}phenoxy) acetic acid (0.200 mg, 0.605 mmol) was dissolved in DMF and cooled on an ice-bath N-(2-Fluorobenzyl) ethanamine (0.102 g, 0.666 mmol), TBTU (0.214 g, 0.666 mmol) and DIPEA (0.22 ml, 1.271 mmol) was added. The reaction mixture was stirred for 16 h at room temperature. EtOAc was added and the organic phase was washed with two portions of 20 ml $NaCO_3$ (sat). The organic layer was dried with $MgSO_4$ and the solvent was removed by evaporation. The crude was purified by preparative HPLC (starting with acetonitrile/buffer 60/40 and then increasing the acetonitrile concentration to 100% acetonitrile in 25 min, the buffer was a mixture of acetonitrile/water 10/90 and ammonium acetate (0.1 M), column KR-100-7-C8, 50*500, flow 80 ml/min). 145 mg of the desired product was obtained after freeze drying (yield 71.1%).

$^1$H-NMR (400 MHz, CD3CO) (rotamers); 1.08, 1.17 (t, t, 3H), 2.96 (s, 3H), 3.07 (m, 2H) 3.31, 3.36 (m, 2H), 4.21 (m, 2H), 4.85 (s, 2H), 4.56-4.82 (m, 2H), 6.18 (d, 1H), 6.88-7.06 (m, 3H), 7.18-7.35 (m, 6H), 7.42 (m, 1H), 7.70 (d, 1H)

f) 2-[2-(4-{2-[ethyl(2-fluorobenzyl)amino]-2-oxoethoxy}phenyl)ethoxy]benzoic acid Methyl 2-[2-(4-{2-[ethyl(2-fluorobenzyl)amino]-2-oxoethoxy}phenyl)ethoxy]benzoate (0.200 g, 0.115 mmol) was dissolved in 3 ml THF in a Smith synthesiser vial and then 1.5 ml water and lithium hydroxide (0.032 g, 1.335 mmol) were added to the vial. The vial was capped and put in the microwave oven (Smith synthesiser). The reaction was then heated to 150° C. for 6 minutes. According to LC-MS the reaction was complete. The solvent was evaporated. The residue was dissolved in diethyl ether (30 ml) and washed with $NaHCO_3$ (sat) (2×20 ml). The basic water layer was acidified to pH 1 with 2M HCl. The water layer was extracted with three portions of 20 ml of DCM which were combined, dried and evaporated to give 160 mg of pure desired product.

$^1$H-NMR (400 MHz, CD3CO) (rotamers); 1.07, 1.15 (t, t, 3H), 3.10 (m, 2H), 3.30, 3.36 (m, m, 2H), 4.21 (m, 2H), 4.55-4.67 (m, 2H), 4.90 (s, 2H), 6.20 (d,1H), 6.87-7.06 (m, 3H), 7.18-7.35 (m, 6H), 7.40(m, 1H), 7.70 (d, 1H)

Example 2 a) 2-Bromo-N-(2,4-difluorobenzyl)-N-heptylacetamide

N-(2,4-difluorobenzyl)-N-heptylamine (2.004 g, 8.304 mmol) was dissolved in DCM (30 ml). It was then cooled in an ice-bath. Triethylamine (1.092 g, 10.796 mmol) was added and then bromacetyl chloride (1.438 g, 9.135 mmol) was dropped in. The mixture was stirred for 2 hours (ice-bath). It was then washed with water (with additional of 1% hydrochloric acid, pH-3), water and brine, and dried (magnesium sulphate) and evaporated. The crude oil product was dissolved in DCM, then loaded onto a column (ISOLUTE®SI 5 g/25 ml) and eluted with more DCM. Oil product 2.412 g was obtained, yield 80%

$^1$H NMR (rotamer, 500 MHz, CDCl$_3$): δ 0.88-0.93 (m, 3H, 1.27-1.34 (m, 8H), 1.52-1.68 (m, 2H), 3.28-3.35 (m, 2H), 3.90-4.15 (m, 2H), 4.61, 4.63 (s, s, 2H), 6.81-6.94 (m, 2H) and 7.15-7.20, 7.34-7.39 (m, 1H).

b) N-(2,4-difluorobenzyl)-N-heptyl-2-[4-(2 hydroxyethyl)-2-methoxyphenoxy]acetamide 2-Bromo-N-(2,4-difluorobenzyl)-N-heptylacetamide (135 mg, 0.373 mmol), homovanillyl alcohol (63 mg, 0.373 mmol) and potassium carbonate anhydrous (77 mg, 0.559 mmol) were mixed in acetonitrile (10 ml). The mixture was heated to reflux for 4 hours and then evaporated to dryness. The residue (with additional DCM, 1 ml×2) was loaded onto a column (ISOLUTE® SI, 1 g/6 ml). It was eluted with DCM and then MeOH/DCM (0.5:99.5, then 1:99). The product fractions were combined and evaporated Oil product 132 mg was obtained yield 79%.

$^1$H NMR (rotamer, 400 MHz, CDCl$_3$): δ 0.82-0.87 (m, 3H), 1.17-1.28 (m, 8H), 1.43-1.68 (m, 2H), 2.75-2.80 (m, 2H), 3.24-3.32 (m, 2H), 3.73-3.84 (m, 5H), 4.58, 4.66 (s, s, 2H), 4.74, 4.76 (s, s, 2H), 6.67-6.86 (m, 5H) and 7.08-7.14, 7.23-7.29 (m, 1H).

c) 2-(4-{2-[(2,4-Difluorobenzyl)(heptyl)amino]-2-oxoethoxy}-3-methoxyphenyl)ethyl methanesulfonate N-(2,4-difluorobenzyl)-N-heptyl-2-[4-(2-hydroxyethyl)-2-methoxyphenoxy]acetamide (A)(132 mg, 0.294 mmol) was dissolved in DCM (10 ml). It was cooled in an ice-bath. Triethylamine (0.05 ml, 0.352 mmol) was added and then methanesulfonyl chloride (37 mg, 0.323 mmol) was dropped in. The cooling-bath was removed after 30 minutes. The mixture was stirred at room temperature overnight. LS-MS showed that ca 50% of A was not reacted. The mixture was cooled in an ice-bath and 0.05 ml of triethylamine was added, followed by 0.025 ml of methanesulfonyl chloride. After addition, the cooling-bath was removed and the mixture was stirred for 5 hours more. It was then washed with water (×2) and brine, dried (magnesium sulphate) and evaporated. Oil product 138 mg was left and used for next step without further purification.

d) Methyl 2-[2-(4-{2-[(2,4-difluorobenzyl)(heptyl) amino]-2-oxoethoxy}-3-methoxyphenyl)ethoxy] benzoate 2-(4-{2-[(2,4-Difluorobenzyl)(heptyl)amino]-2-oxoethoxy}-3-methoxyphenyl)ethyl methanesulfonate (138 mg, 0.262 mmol) was dissolved in acetonitrile (10 ml). 2-Hydroxybenzoic acid methyl ester (40 mg, 0.262 mmol) was added and then potassium carbonate anhydrous (54 mg, 0.392 mmol) was added. The mixture was heated to reflux overnight and then evaporated to dryness. Water (10 ml) and ethyl acetate (10 ml) were added and the two phases were separated. The organic phase was washed with water and brine, dried (magnesium sulphate) and evaporated. Chromatography of the residue on a column (ISOLUTE® SI, 2 g/6 ml) using DCM, MeOH/DCM (1:99) as eluant gave 78 mg the desired product, yield 45% (two steps).

$^1$H NMR (rotamer, 500 MHz, CDCl$_3$): δ 0.87-0.91 (m, 3H), 1.22-1.32 (m, 8H), 1.48-1.63 (m, 2H), 3.09-3.14 (m, 2H), 3.28-3.35 (m, 2H), 3.80, 3.89 (s, s, 3H), 3.89 (s, 3H), 4.21-4.25 (m, 2H), 4.62, 4.71 (s, s, 2H), 4.79, 4.81 (s, s, 2H), 6.77-7.01 (m, 7H), 7.28-7.33 (m, 1H), 7.13-7.18, 7.28-7.33 (m, m, 1H), 7.45 (t, 1H) and 7.81 (d, 1H).

e) 2-[2-(4-{2-[(2,4-Difluorobenzyl(heptyl)amino]-2-oxoethoxy}-3-methoxyphenyl)ethoxy]benzoic acid Methyl 2-[2-(4-{2-[(2,4-difluorobenzyl)(heptyl)amino]-2-oxoethoxy}-3-methoxyphenyl)ethoxy]benzoate (74 mg, 0.127 mmol) dissolved in THF (2 ml) was mixed with lithium hydroxide (6.1 mg, 0.254 mmol) dissolved in water (1 ml). The mixture was irradiated in a microwave oven (Smith Synthesizer) at 150° C. for 8 minutes. LC-MS showed that the reaction was not complete. It was in the oven for additional 10 minutes, LC-MS showed almost no change. 3 mg more of lithium hydroxide was added and thereafter it was in the oven at 150° C. for 8 minutes. LC-MS showed it was still the same as before. 3 mg more of lithium hydroxide and 1 ml water was added. The resulting mixture was in the oven at 150° C. for 10 minutes and LC-MS showed the reaction was complete. It was evaporated to remove THF. The residue was acidified with 1% hydrochloric acid, pH~5, and extracted with ethyl acetate (10 ml). The extracts was dried (magnesium sulphate) and evaporated. Chromatography of the residue on a column (ISOLUTE® SI, 1 g/6 ml) using DCM and then MeOH/DCM (1:99) as eluant gave 60 mg the desired product, yield 83%.

$^1$H NMR (rotamer, 400 MHz, CDCl$_3$): δ 0.82-0.87 (m, 3H), 1.18-1.28 (m, 8H), 1.43-1.61 (m, 2H), 3.10-3.15(m, 2H), 3.24-3.31 (m, 2H), 3.77, 3.85 (s, s, 3H), 4.39-4.44 (m, 2H), 4.59, 4.66 (s, s, 2H), 4.77, 4.78 (s, s, 2H), 6.72-6.91 (m, 5H), 7.01 (d, 1H), 7.09 (t, 1H), 7.10-7.17, 7.26-7.32 (m, m, 1H), 7.51 (t, 1H) and 8.13 (d, 1H).

$^{13}$C NMR (rotamers, 75 MHz, CDCl$_3$): δ 14.07, 22.55, 26.79, 27.02, 28.57, 28.93, 31.70, 35.18, 41.30, 41.34, 44.02, 45.89, 46.99, 55.71, 55.82, 68.19, 68.94, 70.66, 103.38(t), 103.88(t), 111.35(d), 111.39(d), 112.32, 112.41, 112.46, 114.76, 117.64, 119.60(dd), 120.07(dd), 120.53, 122.06, 129.50(dd), 130.54, 130.59, 131.55(dd), 133.60, 134.78, 146.26, 146.39, 149.67, 157.10, 161.60(dd), 160.68 (dd), 161.97(dd), 162.24(dd), 165.12, 167.75 and 167.93.

Example 3 a) N-(4-chlorobenzyl)acetamide

Acetic acid (1.321 g, 22.000 mmol) was dissolved in DMF (10 ml), 1-(4-chlorophenyl)methanamine (2.804 g, 19.800 mmol) was added and the mixture was cooled to 0° C. N-[(1H-1,2,3-benzotriazol-1-yloxy)(dimethylamino)methylene]-N-methylmethanaminium tetrafluoroborate (7.770 g, 24.200 mmol) and N-ethyl-N,N-diisopropylamine (5.971 g, 46.200 mmol) was added. The solution was stirred for two hours at room temperature. EtOAc (20 ml) was added and the organic phase was washed with Na$_2$CO$_3$ (3×20 ml, aq) and HCl (0.5 M, 2×, 10 ml). The organic layer was dried (MgSO$_4$) and the solvent was removed by evaporation. The residue was purified by preparative HPLC (the initial mobile phase was isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product-containing fractions were pooled and the acetonitrile was removed by evaporation. EtOAc (10 ml) was added and the organic phase was washed with two portions of brine and dried (MgSO$_4$) and the solvent was removed by evaporation and gave 2.337 g of N-(4-chlorobenzyl)acetamide (yield 57.8%).

$^1$HNMR (500 MHz, CDCl$_3$): δ 1.96 (s, 3H), 4.31 (d, 2H), 6.46 (bs, 1H), 7.16 (d, 2H), 7.25 (d, 2H).

b) N-(4-chlorobenzyl)-N-ethylamine

N-(4-chlorobenzyl)acetamide (2.337 g, 12.726 mmol) was dissolved in THF (100 ml) and was cooled to zero degrees under argon atmosphere. (Methylthio)methane compound with borane (1:1) (2.417 g, 31.815 mmol) was added and the mixture was refluxed overnight at RT. HCl (15 ml, 10%) was gently added and was stirred overnight. The solvent was removed by evaporation. Diethyl ether (20 ml) was added and the product was extracted to the water phase by K$_2$CO$_3$ (3×15 ml). The aqueous phase was acidified by HCl (10 ml, 10%) and the product was extracted to the organic phase by EtOAc (3×15 ml). The organic phase was dried (MgSO$_4$) and the solvent was removed by evaporation to give 0.938 g of N-(4-chlorobenzyl)-N-ethylamine (yield 43.4%).

$^1$HNMR (500 MHz, CDCl$_3$): δ 1.11 (t, 3H), 2.65 (q, 2H), 3.74 (s, 2H), 7.23-7.28 (m, 4H).

c) Methyl 2-({2-[4-(2-tert-butoxy-2-oxoethoxy)phenyl]ethyl}thio)benzoate

Tert-butyl (4-{2-[(methylsulfonyl)oxy]ethyl}phenoxy)acetate (5.454 g, 17.347 mmol) was dissolved in acetonitrile (100 ml), methyl 2-mercaptobenzoate (3.502 g, 20.816 mmol) and potassium carbonate (4.795 g, 34.694 mmol) was added. The solution was stirred for 10 hours at 60° C. EtOAc (40 ml) was added and the organic phase was washed with two portions of Brine (2×40 ml, aq). The organic layer was dried (MgSO$_4$) and the solvent was removed by evaporation to give 6.931 g of methyl 2-({2-[4-(2-tert-butoxy-2-oxoethoxy)phenyl]ethyl}thio)benzoate. This material was used in the next step without further purification.

d) [4-(2-{[2-(Methoxycarbonyl)phenyl]-thio}ethyl)-phenoxy]acetic acid

Methyl 2-({2-[4-(2-tert-butoxy-2-oxoethoxy)phenyl]ethyl}thio)benzoate (4.630 g, 11.502 mmol) was taken up into DCM (50 ml) and treated with trifluoroacetic acid (44.40 g, 389.405 mmol) at RT for 4 h. The mixture was evaporated and azeotroped with toluene. The crude was purified by preparative HPLC (the initial mobile phase was isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). The solvent was removed by evaporation to give 3.825 g of [4-(2-{[2-(methoxycarbonyl)phenyl]-thio}ethyl)-phenoxy]acetic acid (yield for two steps 63.9% overall).

$^1$HNMR (500 MHz, CDCl$_3$): δ 2.93-2.98 (m, 2H), 3.12-3.17 (m, 2H), 3.92 (s, 3H), 4.67 (s, 2H), 6.88 (d, 2H), 7.13-7.21 (m, 3H), 7.33 (d, 1H), 7.41-7.46 (m, 1H), 7.96 (dd, 1H).

e) Methyl 2-{[2-(4-{2-[(4-chlorobenzyl)(ethyl)amino]-2-oxoethoxy}phenyl)-ethyl]thio}benzoate

[4-(2-{[2-(Methoxycarbonyl)phenyl]thio}ethyl)phenoxy]acetic acid (0.200 g, 0.577 mmol) was dissolved in DMF (10 ml), N-(4-chlorobenzyl)-N-ethylamine (0.108 g, 0.635 mmol) was added and the mixture was cooled to 0° C. N-[(1H-1,2,3-benzotriazol-1-yloxy)(dimethylamino)methylene]-N-methylmethanaminium tetrafluoroborate (0.204 g, 0.635 mmol) and N-ethyl-N,N-diisopropylamine (0.157 g, 1.212 mmol) were added. The solution was stirred overnight at room temperature. Water (100 ml) was added and the water phase was extracted with diethyl ether (3×20 ml). The organic phase was washed with Na$_2$CO$_3$ (3×20 ml, aq) and HCl (0.5 M, 2×, 10 ml). The organic layer was dried (MgSO$_4$) and the solvent was removed by evaporation. The residue was purified by flash chromatography (started with isocratic heptane/EtOAc 30/70 and then the EtOAc concentration was increased to 100%, (silica gel 60 0.004-0.063 mm). The product containing fractions were pooled and the solvent was removed by evaporation to give 0.085 g of methyl 2-{[2-(4-{2-[(4-chlorobenzyl)(ethyl)amino]-2-oxoethoxy}phenyl)ethyl]thio}benzoate (yield 29.6%).

$^1$HNMR (rotamers, 300 MHz, CDCl$_3$): δ 1.09-1.21 (m, 3H), 2.91-2.99 (m, 2H), 3.11-3.18 (m, 2H), 3.32-3.43 (m, 2H), 3.92 (s, 3H), 4.57-4.75 (m, 4H), 6.78, 6.92 (d, d, 2H), 7.12-7.46 (m, 9H), 7.96 (d, 1H).

f) 2-{[2-(4-{2-[(4-chlorobenzyl)(ethyl)amino]-2-oxoethoxy}phenyl)ethyl]thio}benzoic acid Methyl 2-{[2-(4-{2-[(4-chlorobenzyl)(ethyl)amino]-2-oxoethoxy}phenyl)-ethyl]thio}benzoate (0.085 g, 0.170 mmol) was dissolved in a mixture of acetonitrile/water (1/1, 4 ml) and lithium hydroxide (0.008 g, 0.341 mmol) was added. The reaction was performed in an single node microwave oven (5 min. 150 deg). The solvent was removed by evaporation and then HCl (2 ml, 1 M) was added. The water phase was extracted with two portions of EtOAc (20 ml). The combined organic phase was dried (MgSO$_4$) and the solvent was removed by evaporation and gave 0.073 g of 2-{[2-(4-{2-[(4-chlorobenzyl)(ethyl)amino]-2-oxoethoxy}phenyl)ethyl]thio}benzoic acid (yield 88.4%) as an oil which solidified on cooling and standing.

$^1$HNMR (rotamers, 400 MHz, CDCl$_3$): δ 1.09-1.20 (m, 3H), 2.91-2.98 (m, 2H), 3.11-3.17(m, 2H), 3.33-3.42 (m, 2H), 4.58-4.77 (m, 4H), 6.79, 6.92 (d, d, 2H), 7.11-7.49 (m, 9H), 8.10 (d, 1H).

$^{13}$C NMR (rotamers, 100 MHz, CDCl$_3$): δ 12.23, 13.77, 33.70, 33.82, 41.09, 41.30, 47.42, 49.64, 67.37, 67.91, 114.69, 114.81, 123.97-135.58 (complex multiplet), 142.22, 156.45, 156.57, 168.20, 170.63.

The following two Examples were prepared in a similar manner:

Example 4

2-[2-(4-{2-[(4-Chlorobenzyl)(ethyl)amino]-2-oxoethoxy}phenyl)ethoxy]benzoic acid.

Example 5

2-[2-(4-{2-[Ethyl(4-trifluoromethylbenzyl)amino]-2-oxoethoxy}phenyl)ethoxy]benzoic acid.

Example 6 a) Acetic acid (1.321 g, 22.000 mmol) was dissolved in DMF (10 ml), 1-[4-(trifluoromethyl)phenyl]methanamine (3.468 g, 19.800 mmol) was added and the mixture was cooled to 0° C. N-[(1H-1,2,3-benzotriazol-1-yloxy)(dimethylamino)methylene]-N-methylmethanaminium tetrafluoroborate (7.770 g, 24.200 mmol) and N-ethyl-N,N-diisopropylamine (5.971 g, 46.200 mmol) was added. The solution was stirred for two hours at room temperature. EtOAc (20 ml) was added and the organic phase was washed with $Na_2CO3$ (3×20 ml, aq) and HCl (0.5 M, 2×, 10 ml). The organic layer was dried (MgSO4) and the solvent was removed by evaporation. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO4) and the solvent was removed by evaporation and gave 3.085 g of N-[4-(trifluoromethyl)benzyl]acetamide (yield 64.6%).

$^1$HNMR (500 MHz, $CDCl_3$): δ 2.0 (s, 3H), 4.42 (d, 2H), 6.58 (bs, 1H), 7.35 (d, 2H), 7.55 (d, 2H)

b) N-[4-(trifluoromethyl)benzyl]acetamide (3.085 g, 14.204 mmol) was dissolved in THF (100 ml) and was cooled to zero degrees under argon atmosphere. (Methylthio)methane compound with borane (1:1) (2.698 g, 35.511 mmol) was added and the mixture was refluxed over night at RT. HCl (15 ml, 10%) was gently added and was stirred overnight. The solvent was removed by evaporation Diethyl ether (20 ml) was added and the product was extracted to the water phase by $K_2CO_3$ (3×15 ml), the water phase was acidified by HCl (10 ml, 10%) and the product was extracted to the organic phase by EtOAc (3×15 ml). The organic phase was dried ($MgSO_4$) and the solvent was removed by evaporation to give 0.809 g of N-[4-(trifluoromethyl)benzyl]ethanamine (yield 28%).

$^1$HNMR (500 MHz, $CDCl_3$): δ 1.05 (t, 3H), 1.3 (s, 1H), 2.62 (q, 2H), 3.78 (s, 2H), 7.38 (d, 2H), 7.3 (d, 2H)

c) Tert-butyl (4-{2-[(methylsulfonyl)oxy]ethyl}phenoxy) acetate (5.454 g, 17.347 mmol) was dissolved in acetonitrile (100 ml), methyl 2-mercaptobenzoate (3.502 g, 20.816 mmol) and dipotassium carbonate (4.795 g, 34.694 mmol) was added. The solution was stirred for 10 hours at 60° C. EtOAc (40 ml) was added and the organic phase was washed with two portions of Brine (2×40 ml, aq). The organic layer was dried ($MgSO_4$) and the solvent was removed by evaporation to give 6.931 g crude of methyl 2-({2-[4-(2-tert-butoxy-2-oxoethoxy)phenyl]ethyl}thio)benzoate. The crude was used in the next step without further purification.

d) Methyl 2-({2-[4-(2-tert-butoxy-2-oxoethoxy)phenyl] ethyl}thio)benzoate (4.630 g, 11.502 mmol) was take up in DCM (50 ml) and treated with trifluoroacetic acid (44.40 g, 389.405 mmol) at r.t for 4 h. The mixture was evaporated and azeotroped with toluene. The crude was purified by preparative HPLC (started with isocratic acetonitrile/buffer 60/40 and then the acetonitrile concentration was increased to 100%, the buffer was a mixture of acetonitile/water 10/90 and ammonium acetate (0.1 M, column KR-100-7-C8, 50 mm×250 mm, flow 40 ml/min). The product containing fractions was pooled and the acetonitrile was removed by evaporation. EtOAc (10 ml) was added and the organic phase was washed with two potions of brine and dried (MgSO4). The solvent was removed by evaporation to give 3.825 g of [4-(2-{[2-(methoxycarbonyl)phenyl]thio}ethyl) phenoxy]-acetic acid (yield for two steps 63.9% overall).

$^1$HNMR (500 MHz, $CDCl_3$): δ 2.82 (t, 2H), 3.15 (t, 2H), 3.82 (s, 3H), 4.35 (s, 2H), 6.78 (d, 2H), 7.18 (d, 2H), 7.23 (t, 1H), 7.51 (d, 1H), 7.55 (t, 1H), 7.85 (d, 1H).

e) [4-(2-{[2-(methoxycarbonyl)phenyl]thio}ethyl)phenoxy]acetic acid (0.200 g, 0.577 mmol) was dissolved in DMF (10 ml), N-[4-(trifluoromethyl)benzyl]ethanamine (0.129 g, 0.635 mmol) was added and the mixture was cooled to 0° C. N-[(1H-1,2,3-benzotriazol-1-yloxy)(dimethylamino)methylene]-N-methylmethanaminium tetrafluoroborate (0.204 g, 0.635 mmol) and N-ethyl-N,N-diisopropylamine (0.157 g, 1.212 mmol) was added. The solution was stirred overnight at room temperature. Water (100 ml) was added and the water phase was extracted with diethyl ether (3×20 ml). The organic phase was washed with $Na_2CO_3$ (3×20 ml, aq) and HCl (0.5 M, 2×, 10 ml). The organic layer was dried (MgSO4) and the solvent was removed by evaporation. The crude was purified by flash chromatography (started with isocratic heptane/EtOAc 30/70 and then the EtOAc concentration was increased to 100%, (silica gel 60 0.004-0.063 mm). The product containing fractions were pooled and the solvent was removed by evaporation to give 0.085 g of methyl 2-({2-[4-(2-{ethyl [4-(trifluoromethyl)benzyl]amino}-2-oxoethoxy)phenyl] ethyl}thio)benzoate (yield 27.7%).

$^1$HNMR (Rotamers, 500 MHz, $CDCl_3$): δ 1.1-1.23 (bm, 3H), 2.95 (q, 2H), 3.15 (q, 2H), 3.42 (m, 2H), 3.9 (s, 3H), 4.7-4.82 (bm, 4H), 6.75-6.95 (m, 2H), 7.1-7.5 (m, 9H), 7.97 (d, 1H).

f) Methyl 2-({2-[4-(2-{ethyl[4-(trifluoromethyl)benzyl] amino}-2-oxoethoxy)phenyl]-ethyl}thio)benzoate (0.085 g, 0.160 mmol) was dissolved in a mixture of acetonitrile/ water (1/1, 4 ml), then lithium hydroxide (0.008 g, 0.320 mmol) was added. The reaction was performed in an single node microwave oven (5 min, 150 deg). Work-up by removing the solvent by evaporation and addition of HCl (2 ml, 1 M). The water phase was extracted with two portions of EtOAc (20 ml), the organic phase was dried ($MgSO_4$) and the solvent was removed by evaporation and gave 0.07773 g of 2-({2-[4-(2-{ethyl[4-(trifluoromethyl)benzyl]amino}-2-oxoethoxy)phenyl]ethyl}thio)benzoic acid (yield 93.0%).

$^1$HNMR (Rotamers, 400 MHz, $CDCl_3$): δ 1.02-1.25 (bm, 3H), 2.95 (q, 2H), 3.15 (q, 2H), 3.38 (m, 2H), 4.60-4.82 (bm, 4H), 6.75-6.95 (m, 2H), 7.1-7.5 (m, 9H), 7.97 (d, 1H).

Example 7

Methyl 2-{2-[4-(2-{butyl[2-fluoro-4-(trifluoromethyl) benzyl]amino}-2-oxoethoxy)phenyl]ethoxy}benzoate (0.230 g, 0.410 mmol) was dissolved in a mixture of THF/water (1/1, 4 ml). Lithium hydroxide (0.015 g, 0.617 mmol) was added. The reaction was performed in an single node microwave oven (14 min, 150 deg). Work-up by removing the solvent by evaporation and addition of HCl (2 ml, 1 M). The water-phase was extracted with two portions of EtOAc (20 ml). The organic phase was dried (MgSO4) and the solvent was removed by evaporation to give 0.212 g of 2-{2-[4-(2-{butyl[2-fluoro-4-(trifluoromethyl)benzyl]amino}-2-oxoethoxy)phenyl]ethoxy}benzoic acid (yield 94.5%).

$^1$HNMR (Rotamers, 500 MHz, CDCl$_3$): δ 0.82-1.0 (bm, 3H), 1.2-1.4 (bm, 2H), 1.65-1.7 (bm, 2H), 3.13 (m, 2H), 3.32 (m, 2H), 4.4 (m, 2H), 4.63-4.8 (M, 4H), 6.7-7.6 (bm, 10H), 8.1 (d, 1H).

Example 8 a) (4-{2-[2-(Methoxycarbonyl)phenoxy]ethyl}phenoxy)acetic acid (0.150 g, 0.454 mmol) was dissolved in DMF (10 ml), N-(2,4-difluorobenzyl)-N-propylamine (0.084 g, 0.454 mmol) was added and the mixture was cooled to 0° C. N-[(1H-1,2,3-benzotriazol-1-yloxy)(dimethylamino)methylene]-N-methylmethanaminium tetrafluoroborate (0.160 g, 0.499 mmol) and N-ethyl-N,N-diisopropylamine (0.123 g, 0.954 mmol) was added. The solution was stirred for two hours at room temperature. EtOAc (20 ml) was added and the organic phase was washed with Na$_2$CO3 (3×20 ml, aq) and HCl (0.5 M, 2×10 ml). The organic layer was dried (MgSO4) and the solvent was removed by evaporation to give 0.220 g of methyl 2-[2-(4-{2-[(2,4-difluorobenzyl)(propyl)amino]-2-oxoethoxy}phenyl)-ethoxy]benzoate (yield 97.4%).

$^1$HNMR (Rotamers, 500 MHz, CDCl$_3$): δ 0.8-1.0 (bm, 3H), 1.45-1.7 (bm, 2H) 3.1 (m, 2H), 3.28 (bm, 2H), 3.9 (s, 3H), 4.2 (q, 2H), 4.6-4.75 (M, 4H), 6.7-7.0 (bm, 6H), 7.1-7.3 (bm, 3H), 7.4 (m, 1H), 7.78 (d, 1H).

b) Methyl 2-[2-(4-{2-[(2,4-difluorobenzyl)(propyl)amino]-2-oxoethoxy}phenyl)-ethoxy]benzoate (0.22 g, 0.442 mmol) was dissolved in a mixture of THF/water (1/1, 4 ml). Lithium hydroxide (0.021 g, 0.884 nmol) was added. The reaction was performed in an single node microwave oven (14 min, 150 deg). Work-up by removing the solvent by evaporation and addition of HCl (2 ml, 1 M). The waterphase was extracted with two portions of EtOAc (20 ml), the organic phase was dried (MgSO4) and the solvent was removed by evaporation to give 0.180 g of 2-[2-(4-{2-[(2,4-difluorobenzyl)(propyl)-amino]-2-oxoethoxy}phenyl)ethoxy]benzoic acid (yield 84.2%).

$^1$HNMR (Rotamers, 500 MHz, CDCl$_3$): δ 0.8-1.0 (bm, 3H), 1.45-1.7 (bm, 2H), 3.14 (m, 2H), 3.28 (bm, 2H), 4.4 (q, 2H), 4.62 (s, 2H), 4.75 (s, 2H), 6.7-7.35 (bm, 9H), 7.52 (t, 1H), 8.12 (d, 1H).

Example 9 a) (4-{2-[2-(methoxycarbonyl)phenoxy]ethyl}phenoxy)acetic acid (0.150 g, 0.454 mmol) was dissolved in DMF (10 ml), N-benzyl-N-ethylamine (0.061 g, 0.454 mmol) was added and the mixture was cooled to 0° C. N-[(1H-1,2,3-benzotriazol-1-yloxy)-(dimethylamino)methylene]-N-methylmethanaminium tetrafluoroborate (0.160 g, 0.499 mmol) and N-ethyl-N,N-diisopropylamine (0.123 g, 0.954 mmol) was added. The solution was stirred for two hours at room temperature. EtOAc (20 ml) was added and the organic phase was washed with Na$_2$CO3 (3×20 ml, aq) and HCl (0.5 M, 2×, 10 ml). The organic layer was dried (MgSO4) and the solvent was removed by evaporation to give 0.138 g of methyl 2-[2-(4-{2-[benzyl(ethyl)amino]-2-oxoethoxy}phenyl)ethoxy]benzoate (yield 67.9%).

$^1$HNMR (Rotamers, 500 MHz, CDCl$_3$): δ 1.07-1.22 (bm, 3H), 3.1 (m, 2H), 3.20 (bm, 2H), 3.9 (s, 3H), 4.2 (q, 2H), 4.6-4.8 (M, 4H), 6.8-7.02 (bm, 4H), 6.18-7.5 (bm, 8H), 7.78 (d, 1H).

b) Methyl 2-[2-(4-{2-[benzyl(ethyl)amino]-2-oxoethoxy}phenyl)ethoxy]benzoate (0.138 g, 0.308 mmol) was dissolved in a mixture of THF/water (1/1, 4 ml). Lithium hydroxide (0.015 g, 0.617 mmol) was added. The reaction was performed in an single node microwave oven (14 min, 150 deg). Workup by removing the solvent by evaporation and addition of HCl (2 ml, 1 M). The waterphase was extracted with two portions of EtOAc (20 ml), the organic phase was dried (MgSO4) and the solvent was removed by evaporation to give 0.146 g of 2-[2-(4-{2-[benzyl(ethyl)amino]-2-oxoethoxy}phenyl)ethoxy]benzoic acid.

$^1$HNMR (Rotamers, 500 MHz, CDCl$_3$): δ 1.02-1.22 (bm, 3H), 3.1 (m, 2H), 3.25-3.5 (bm, 2H), 4.2 (q, 2H), 4.55-4.8 (M, 4H), 6.8-7.4 (bm, 11H), 7.5 (m, 1H), 8.1 (d, 1H).

Example 10 a) Tert-butyl (4-{2-[(methylsulfonyl)oxy]ethyl}phenoxy)acetate (5.454 g, 17.347 mmol) was dissolved in acetonitrile (100 ml), methyl 2-mercaptobenzoate (3.502 g, 20.816 mmol) and dipotassium carbonate (4.795 g, 34.694 mmol) was added. The solution was stirred for 10 hours at 60° C. EtOAc (40 ml) was added and the organic phase was washed with two portions of brine (2×40 ml, aq). The organic layer was dried (MgSO$_4$) and the solvent was removed by evaporation to give 6.931 g crude of methyl 2-({2-[4-(2-tert-butoxy-2-oxoethoxy)phenyl]ethyl}thio)benzoate. The crude was used in the next step without further purification.

b) Methyl 2-({2-[4-(2-tert-butoxy-2-oxoethoxy)phenyl]ethyl}thio)benzoate (4.630 g, 11.502 mmol) was take up in DCM (50 ml) and treated with trifluoroacetic acid (44.40 g, 389.405 mmol) at r.t for 4 h. The mixture was evaporated and azeotroped with toluene. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO$_4$). The solvent was removed by evaporation to give 3.825 g of [4-(2-{[2-(methoxycarbonyl)phenyl]thio}ethyl)-phenoxy]acetic acid (yield for two steps 63.9% overall).

$^1$HNMR (500 MHz, CDCl$_3$): δ 2.82 (t, 2H), 3.15 (t, 2H), 3.82 (s, 3H), 4.35 (s, 2H), 6.78 (d, 2H), 7.18 (d, 2H), 7.23 (t, 1H), 7.51 (d, 1H), 7.55 (t, 1H), 7.85 (d, 1H).

c) [4-(2-{[2-(methoxycarbonyl)phenyl]thio}ethyl)phenoxy]acetic acid (0.200 g, 0.577 mmol) was dissolved in DMF (10 ml), N-benzyl-N-ethylamine (0.086 g, 0.635 mmol) was added and the mixture was cooled to 0° C. N-[(1H-1,2,3-benzotriazol-1-yloxy)(dimethylamino)methylene]-N-methylmethanaminium tetrafluoroborate (0.204 g, 0.635 mmol) and N-ethyl-N,N-diisopropylamine (0.157 g, 1.212 mmol) was added. The solution was stirred over night at room temperature. Water (100 ml) was added and the water phase was extracted with diethyl ether (3×20 ml). The organic phase was washed with Na$_2$CO$_3$ (3×20 ml, aq) and HCl (0.5 M, 2×, 10 ml). The organic layer was dried (MgSO4) and the solvent was removed by evaporation. The crude was purified by flash chromatography (started with isocratic heptane/EtOAc 30/70 and then the EtOAc concentration was increased to 100%, (silica gel 60 0.004-0.063 mm). The product containing fractions were pooled and the solvent was removed by evaporation to give 0.137 g of methyl 2-{[2-(4-{2-[benzyl(ethyl)amino]-2-oxoethoxy}phenyl)-ethyl]thio}benzoate (yield 51.2%).

d) Methyl 2-{[2-(4-{2-[benzyl(ethyl)amino]-2-oxoethoxy}phenyl)ethyl]thio}benzoate (0.137 g, 0.296 mmol) was dissolved in a mixture of acetonitrile/water (1/1, 4 ml), lithium hydroxide (0.014 g, 0.591 mmol) was added. The reaction was performed in an single node microwave oven (5 min, 150 deg). Work-up by removing the solvent by evaporation and addition of HCl (2 ml, 1 M). The waterphase was extracted with two portions of EtOAc (20 ml), the organic phase was dried (MgSO$_4$) and the solvent was removed by evaporation and gave 0.111 g of 2-{[2-(4-{2[-benzyl(ethyl)amino]-2-oxoethoxy}phenyl)ethyl]-thio}benzoic acid (yield 83.5%).

$^1$HNMR (Rotamers, 400 MHz, CDCl$_3$): δ 1.02-1.30 (bm, 3H), 2.95 (q, 2H), 3.15 (q, 2H), 3.40 (m, 2H), 4.58 (s, 2H), 4.63-4.92 (bm, 4H), 6.85-7.0 (bm, 2H), 7.0-7.53 (m, 10H), 7.97 (d, 1H).

Example 11 a) N-(4-tert-butylbenzyl)-N-ethylamine (0.143 g, 0.746 mmol) was dissolved in dry acetonitrile under N$_2$ and N-ethyl-N,N-diisopropylamine (0.371 g, 2.867 mmol) was added. The mixture was stirred for 30 min and methyl 2-{2-[4-(2-chloro-2-oxoethoxy)phenyl]ethoxy}benzoate (0.200 g, 0.573 mmol) was added. The solution was stirred overnight at room temperature. The crude was purified by flash cromatography (started with isocratic heptane/EtOAc 50/50 and then the EtOAc concentration was increased to 100%, (silica gel 60 0.004-0.063 mm). The product containing fractions were pooled and the EtOAc was removed by evaporation to give 0.229 g of methyl 2-[2-(4-{2-[(4-tert-butylbenzyl)(ethyl)amino]-2-oxoethoxy}phenyl)ethoxy]benzoate (yield 79.3%).

$^1$HNMR (Rotamers, 500 MHz, CDCl$_3$): δ 1.07-1.23 (bm, 3H), 2.23 (m, 9H), 3.08 (m, 2H), 3.30-3.5 (bm, 2H), 3.87 (s, 3H), 4.18 (m, 2H), 4.58 (d, 2H), 4.63-4.8 (m, 2H) 6.77-7.43 (m, 11H), 7.78 (d, 1H).

b) Methyl 2-[2-(4-{2-[(4-tert-butylbenzyl)(ethyl)amino]-2-oxoethoxy}phenyl)-ethoxy]benzoate (0.2290 g, 0.455 mmol) was dissolved in a mixture of THF (freshly distilled)/water (2/1, 3 ml), lithium-hydroxide (0.218 g, 0.909 mmol) was added. The reaction was performed in a single node microwave oven (5 min, 150 deg). THF was removed by evaporation. Water was added (10 ml) and the basic water phase was washed with diethyl ether (2×10 ml). Addition of HCl (2 ml, 1 M, pH 1). The water phase was extracted with two portions of DCM (20 ml), the organic phase was dried (MgSO4) and the solvent was removed by evaporation to give 0.163 g of 2-[2-(4-{2-[(4-tert-butylbenzyl)(ethyl)amino]-2-oxoethoxy}phenyl)ethoxy]benzoic acid (yield 73.2%).

$^1$HNMR (Rotamers, 500 MHz, CDCl$_3$): δ 1.07-1.21 (bm, 3H), 2.28 (m, 9H), 3.12 (m, 2H), 3.28-3.5 (bm, 2H), 4.4 (m, 2H), 4.58 (d, 2H), 4.63-4.78 (m, 2H) 6.80-7.55 (m, 11H), 8.1 (d, 1H).

Example 12 a) Acetic acid (1.321 g, 22.000 mmol) was dissolved in DMF (10 ml), 1-(4-fluorophenyl)methanamine (2.478 g, 19.800 mmol) was added and the mixture was cooled to 0° C. N-[(1H-1,2,3-benzotriazol-1-yloxy)(dimethylamino)methylene]-N-methylmethanaminium tetrafluoroborate (7.770 g, 24.200 mmol) and N-ethyl-N,N-diisopropylamine (5.971 g, 46.200 mmol) was added. The solution was stirred for two hours at room temperature. EtOAc (20 ml) was added and the organic phase was washed with Na$_2$CO3 (3×20 ml, aq) and HCl (0.5 M, 2×, 10 ml). The organic layer was dried (MgSO4) and the solvent was removed by evaporations. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions was pooled and the acetonitrile was removed by evaporation. EtOAc (10 ml) was added and the organic phase was washed with two portions of brine and dried (MgSO4) and the solvent was removed by evaporation and gave 1.344 g of N-(4-fluorobenzyl)acetamide (yield 36.5%).

$^1$HNMR (500 MHz, CDCl$_3$): δ 1.98 (s, 3H), 4.35 (d, 2H), 6.25 (bs, 1H), 6.95-7.25 (bm, 4H)

b) N-(4-Fluorobenzyl)acetamide (1.344 g, 8.039 mmol) was dissolved in THF (100 ml) and was cooled to zero degrees under argon atmosphere. (Methylthio)methene compound with borane (1:1) (1.527 g, 20.098 mmol) was added and the mixture was refluxed overnight at RT. HCl (15 ml, 10%) was gently added and was stirred overnight. The solvent was removed by evaporation. Diethyl ether (20 ml) was added and the product was extracted to the water phase by K$_2$CO$_3$ (3×15 ml). The water phase was acidified by HCl (10 ml, 10%) and the product was extracted to the organic phase by EtOAc (3×15 ml). The organic phase was dried (MgSO$_4$) and the solvent was removed by evaporation to give 0.309 g of N-(4-fluorobenzyl)ethanamine (yield 25.1%).

$^1$HNMR (400 MHz, CDCl$_3$): δ 1.05 (t, 3H), 1.1 (s, 1H), 2.58 (q, 2H), 3.64 (s, 2H), 6.9 (t, 2H), 7.2 (t, 2H).

c) N-(4-Fluorobenzyl)ethanamine (0.114 g, 0.745 mmol) was dissolved in dry acetonitrile under N$_2$ and N-ethyl-N,N-diisopropylamine (0.371 g, 2.867 nmol) was added. The mixture was stirred for 30 min and methyl 2-{2-[4-(2-chloro-2-oxoethoxy)phenyl]-ethoxy}benzoate (0.200 g, 0.573 mmol) was added. The solution was stirred overnight at room temperature. The crude was purified by flash chromatography (started with isocratic heptane/EtOAc 50/50 and then the EtOAc concentration was increased to 100%, (silica gel 60 0.004-0.063 mm). The product containing fractions were pooled and the EtOAc was removed by evaporation to give 0.223 g of methyl 2-[2-(4-{2-[ethyl(4-fluorobenzyl)amino]-2-oxoethoxy}phenyl)ethoxy]benzoate (yield 83.5%).

$^1$HNMR (Rotamers, 500 MHz, CDCl$_3$): δ 1.07-1.23 (bm, 3H), 3.08 (m, 2H), 3.30-3.45 (bm, 2H), 3.87 (s, 3H), 4.18 (m, 2H), 4.58 (s, 2H), 4.63-4.8 (m, 2H) 6.77-7.45 (m, 11H), 7.78 (d, 1H).

d) Methyl 2-[2-(4-{2-[ethyl(4-fluorobenzyl)amino]-2-oxoethoxy}phenyl)ethoxy]-benzoate (0.223 g, 0.479 mmol) was dissolved in a mixture of THF (freshly distilled)/water (2/1, 3 ml), lithium hydroxide (0.229 g, 0.958 mmol) was added. The reaction was performed in a single node microwave oven (5 min, 150 deg). THF was removed by evaporation. Water was added (10 ml) and the basic water phase was washed with diethyl ether (2×10 ml). Addition of HCl (2 ml, 1 M, pH 1). The water phase was extracted with two portions of DCM (20 ml), the organic phase was dried (MgSO4) and the solvent was removed by evaporation to give 0.196 g of 2-[2-(4-{2-[ethyl(4-fluorobenzyl)amino]-2-oxoethoxy}phenyl)ethoxy]benzoic acid (yield 90.6%).

$^1$HNMR (Rotamers, 500 MHz, CDCl$_3$): δ 1.03-1.21 (bm, 3H), 3.1 (m, 2H), 3.23-3.4 (bm, 2H), 4.38 (m, 2H), 4.55 (s, 2H), 4.63-4.78 (m, 2H), 6.75-7.22 (m, 10H), 7.47 (t, 1H), 8.07 (d, 1H).

Example 13 a) Tert-butyl (4-{2-[(methylsulfonyl)oxy]ethyl}phenoxy) acetate (5.454 g, 17.347 mmol) was dissolved in acetonitrile (100 ml), methyl 2-mercaptobenzoate (3.502 g, 20.816 mmol) and dipotassium carbonate (4.795 g, 34.694 mmol) was added. The solution was stirred for 10 hours at 60° C. EtOAc (40 ml) was added and the organic phase was washed with two portions of Brine (2×40 ml, aq). The organic layer was dried (MgSO$_4$) and the solvent was removed by evaporation to give 6.931 g crude of methyl 2-({2-[4-(2-tert-butoxy-2-oxoethoxy)phenyl]ethyl}thio)benzoate. The crude was used in the next step without further purification.

b) Methyl 2-({2-[4-(2-tert-butoxy-2-oxoethoxy)phenyl] ethyl}thio)benzoate (4.630 g, 11.502 mmol) was take up in DCM (50 ml) and treated with trifluoroacetic acid (44.40 g, 389.405 mmol) at r.t for 4 h. The mixture was evaporated and azeotroped with toluene. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO4). The solvent was removed by evaporation to give 3.825 g of [4-(2-{[2-(methoxycarbonyl)phenyl]thio}ethyl) phenoxy]-acetic acid (yield for two steps 63.9% overall).

$^1$HNMR (500 MHz, CDCl$_3$): δ 2.82 (t, 2H), 3.15 (t, 2H), 3.82 (s, 3H), 4.35 (s, 2H), 6.78 (d, 2H), 7.18 (d, 2H), 7.23 (t, 1H), 7.51 (d, 1H), 7.55 (t, 1H), 7.85 (d, 1H).

c) [4-(2-{[2-(Methoxycarbonyl)phenyl]thio}ethyl)phenoxy]acetic acid (0.250 g, 0.722 mmol) was dissolved in DCM (10 ml), N-(2-fluorobenzyl)ethanamine (0.105 g, 0.686 mmol) was added. N-[(1H-1,2,3-benzotriazol-1-yloxy)(dimethylamino)methylene]-N-methylmethanaminium tetrafluoroborate (0.255 g, 0.0.794 mmol) and N-ethyl-N,N-diisopropylamine (0.187 g, 1.443 mmol) were added. The solution was stirred for 2 hours at room temperature. The crude was purified by flash chromatography (started with isocratic DCM 100% and then the MeOH concentration was increased from 0.5% to 20%, (silica gel 60 0.004-0.063 mm). The product containing fractions were pooled and the EtOAc was removed by evaporation. The substance needed to be purified once more and it was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. The ammonium acetate was removed by freeze drying the product overnight to give 0.1 g of methyl 2-{[2-(4-{2-[ethyl(2-fluorobenzyl)amino]-2-oxoethoxy}phenyl)ethyl]thio}benzoate (yield 29.1%).

$^1$HNMR (Rotamers, 500 MHz, CDCl$_3$): δ 1.03-1.23 (bm, 3H), 2.95 (q, 2H), 3.15 (q, 2H), 3.40 (m, 2H), 3.9 (s, 3H), 4.6-4.8 (bm, 4H), 6.75-6.95 (m, 2H), 6.97-7.5 (m, 9H), 7.97 (d, 1H).

d) Methyl 2-{[2-(4-{2-[ethyl(2-fluorobenzyl)amino]-2-oxoethoxy}phenyl)ethyl]thio}-benzoate was dissolved in a mixture of THF (freshly distilled)/water (2/1, 3 ml), Lithium hydroxide (0.015 g, 0.629 mmol) was added. The reaction was performed in a single node microwave oven (5 min, 150 deg). THF was removed by evaporation. Water was added (10 ml) and the basic water phase was washed with diethyl ether (2×10 ml). Addition of HCl (2 ml, 1 M, pH 1). The water phase was extracted with two portions of DCM (20 ml), the organic phase was dried (MgSO4) and the solvent was removed by evaporation to give 0.095 g of 2-{[2-(4-{2-[ethyl(2-fluorobenzyl)amino]-2-oxoethoxy}phenyl) ethyl]-thio}benzoic acid (yield 96.9%)

$^1$HNMR (Rotamers, 400 MHz, CDCl$_3$): δ 1.02-1.25 (bm, 3H), 2.95 (q, 2H), 3.15 (q, 2H), 3.42 (m, 2H), 4.60-4.80 (bm, 4H), 6.75-6.95 (m, 2H), 6.95-7.5 (m, 9H), 8.1 (d, 1H).

Example 14 a) Tert-butyl (4-{2-[(methylsulfonyl)oxy]ethyl}phenoxy) acetate (5.454 g, 17.347 mmol) was dissolved in acetonitrile (100 ml), methyl 2-mercaptobenzoate (3.502 g, 20.816 mmol) and dipotassium carbonate (4.795 g, 34.694 mmol) was added. The solution was stirred for 10 hours at 60° C. EtOAc (40 ml) was added and the organic phase was washed with two portions of brine (2×40 ml, aq). The organic layer was dried (MgSO$_4$) and the solvent was removed by evaporation to give 6.931 g crude of methyl 2-({2-[4-(2-tert-butoxy-2-oxoethoxy)phenyl]ethyl}thio)benzoate. The crude was used in the next step without further purification.

b) Methyl 2-({2-[4-(2-tert-butoxy-2-oxoethoxy)phenyl] ethyl}thio)benzoate (4.630 g, 11.502 mmol) was take up in DCM (50 ml) and treated with trifluoroacetic acid (44.40 g, 389.405 mmol) at r.t for 4 h. The mixture was evaporated and azeotroped with toluene. The crude was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. EtOAc (10 ml) was added and the organic phase was washed with two portions of brine and dried (MgSO4). The solvent was removed by evaporation to give 3.825 g of [4-(2-{[2-(methoxycarbonyl)phenyl]thio}ethyl-) phenoxy]acetic acid (yield for two steps 63.9% overall).

$^1$HNMR (500 MHz, CDCl$_3$): δ 2.82 (t, 2H), 3.15 (t, 2H), 3.82 (s, 3H), 4.35 (s, 2H), 6.78 (d, 2H), 7.18 (d, 2H), 7.23 (t, 1H), 7.51 (d, 1H), 7.55 (t, 1H), 7.85 (d, 1H).

c) [4-(2-{[2-(methoxycarbonyl)phenyl]thio}ethyl)phenoxy]acetic acid (0.250 g, 0.722 mmol) was dissolved in DCM (10 ml) and N-(2-chlorobenzyl)-N-ethylamine (0.116 g, 0.686 mmol) was added. N-[(1H-1,2,3-Benzotriazol-1-yloxy)(dimethylamino)methylene]-N-methylmethanaminium tetrafluoroborate (0.255 g, 0.0.794 mmol) and N-ethyl-N,N-diisopropylamine (0.187 g, 1.443 mmol) were added. The solution was stirred for 2 hours at room temperature. The crude was purified by flash chromatography (started with isocratic DCM 100% and then the MeOH concentration was increased from 0.5% to 20%, (silica gel 60 0.004-0.063 mm). The product containing fractions were pooled and the EtOAc was removed by evaporation. The substance needed to be purified once more and it was purified by preparative HPLC (started with isocratic acetonitrile/buffer 60/40 and then the acetonitrile concentration was increased to 100%, the buffer was a mixture of acetonitrile/water 10/90 and ammonium acetate (0.1 M, column KR-100-7-C8, 50 mm×250 mm, flow 40 ml/min). The product containing fractions were pooled and the acetonitrile was removed by evaporation. The ammonium acetate was removed by freeze drying the product overnight to give 0.111 g of methyl 2-{[2-(4-{2-[(2-chlorobenzyl)(ethyl)amino]-2-oxoethoxy}phenyl)ethyl]thio}benzoate (yield 30.9%).

$^1$HNMR (Rotamers, 500 MHz, CDCl$_3$): δ 1.10-1.25 (bm, 3H), 2.95 (m, 2H), 3.15 (m, 2H), 3.40 (m, 2H), 3.9 (s, 3H), 4.64-8 (bm, 4H), 6.75-6.95 (m, 2H), 7.02-7.5 (m, 9H), 7.95 (d, 1H).

d) Methyl 2-{[2-(4-{2-[(2-chlorobenzyl)(ethyl)amino]-2-oxoethoxy}phenyl)ethyl]thio}-benzoate was dissolved in a mixture of THF (freshly distilled)/water (2/1, 3 ml), Lithium hydroxide (0.015 g, 0.629 mmol) was added. The reaction was performed in a single node microwave oven (5 min, 150 deg). THF was removed by evaporation. Water was added (10 ml) and the basic water phase was washed with diethyl ether (2×10 ml). Addition of HCl (2 ml, 1 M, pH 1). The water phase was extracted with two portions of DCM (20 ml). The organic phase was dried (MgSO4) and the solvent was removed by evaporation to give 0.103 g of 2-{[2-(4-{2-[(2-chlorobenzyl)(ethyl)amino]-2-oxoethoxy}phenyl)ethyl]thio}-benzoic acid (yield 95.5%).

$^1$HNMR (Rotamers, 400 MHz, CDCl$_3$): δ 1.07-1.25 (bm, 3H), 2.95 (m, 2H), 3.15 (m, 2H), 3.42 (m, 2H), 4.62-4.85 (bm, 4H), 6.75-6.95 (m, 2H), 7.02-7.5 (m, 9H), 8.1 (d, 1H).

Biological Activity

Formulations

Compounds were dissolved in DMSO to obtain 16 mM stock solutions. Before assays, stock solutions were further diluted in DMSO and culture media.

General Chemicals and Reagents

Luciferase assay reagent was purchased from Packard, USA. Restriction Enzymes were from Boehringer and Vent polymerase from New England Biolabs.

Cell Lines and Cell Culture Conditions

U2-OS, (Osteogenic sarcoma, Human) was purchased from ATCC, USA. Cells were expanded and refrozen in batches from passage number six. Cells were cultured in Dulbecco's modified Eagle medium (DMEM) with 25 mM glucose, 2 mM glutamine or 4 mM L-alanyl-L-glutamine, 10% fetal calf serum, at 5% CO$_2$. Phosphate buffered saline (PBS) without addition of calcium or magnesium was used. All cell culture reagents were from Gibco (USA) and 96-well cell culture plates were purchased from Wallach.

Plasmid Constructs for Heterologous Expression

Standard recombinant DNA techniques were carried out as described by Ausubel (7). The Luciferase reporter vector, pGL5UAS (clone consists of five copies of the GAL4 DNA binding sequence, 5'-CGACGGAGTACTGTCCTC-CGAGCT-3', cloned into the SacI/XhoI sites of pGL3-Promoter (Promega). The SacI/XhoI fragment carrying the UAS sites was constructed using annealed overlapping oligonucleotides.

Expression vectors used are based upon pSG5 (Stratagene). All vectors contain an EcoRI/NheI fragment encoding the DNA binding domain of GAL4 (encoding amino acid positions 1-145 of database accession number P04386) followed by an in-frame fusion to a fragment encoding the nuclear localisation sequence from T antigen of Polyoma Virus. The nuclear localisation sequence was constructed using annealed overlapping oligonucleotides creating NheI/KpnI sticky ends (5'-CTAGCGCTCCTAGAAGAAACG-CAAGGTTGGTAC-3'). The ligand binding domains from human and mouse PPARα and human and mouse PPARγ were PCR amplified as KpnI/BamHI fragments and cloned in frame to the GAL4 DNA binding domain and the nuclear localisation sequence. The sequence of all plasmid constructs used were confirmed by sequencing.

The following expression vectors were used for transient transfections:

| vector | encoded PPAR subtype | sequence reference[1] |
|---|---|---|
| pSGGALhPPa | human PPARα | S74349, nt 625–1530 |
| pSGGALmPPa | murine PPARα | X57638, nt 668–1573 |
| pSGGALhPPg | human PPARγ | U63415, nt 613–1518 |
| pSGGALmPPg | murine PPARγ | U09138, nt 652–1577 |

[1]refers to nucleotide positions of data base entry used to express the ligand binding domain.

Transient Transfections

Frozen stocks of cells from passage number six were thawed and expanded to passage number eight before transfections. Confluent cells were trypsinised, washed and pelleted by centrifugation at 270×g for 2 minutes. The cell pellet was resuspended in cold PBS to a cell concentration of about 18×10$^6$ cells/ml. After addition of DNA, the cell suspension was incubated on ice for approximately 5 minutes before electroporation at 230 V, 960 μF in Biorad's Gene Pulser™ in 0.5 ml batches. A total of 50 μg DNA was added to each batch of 0.5 ml cells, including 2.5 μg expression vector, 25 μg reporter vector and 22.5 μg unspecific DNA (pBluescript, Stratagene).

After electroporation, cells were diluted to a concentration of 320,000 cells/ml in DMEM without phenol red, and approximately 25,000 cells/well were seeded in 96-well plates. In order to allow cells to recover, seeded plates were incubated at 37° C. for 3-4 hours before addition of test compounds. In assays for PPARα, the cell medium was supplemented with resin-charcoal stripped fetal calf serum (FCS) in order to avoid background activation by fatty acid components of the FCS. The resin-charcoal stripped FCS was produced as follows; for 500 ml of heat-inactivated FCS, 10 g charcoal and 25 g Bio-Rad Analytical Grade Anion Exchange Resin 200-400 mesh were added, and the solution was kept on a magnetic stirrer at room temperature over night. The following day, the FCS was centrifuged and the stripping procedure was repeated for 4-6 hours. After the second treatment, the FCS was centrifuged and filter sterilised in order to remove remnants of charcoal and resin.

Assay Procedure

Stock solutions of compounds in DMSO were diluted in appropriate concentration ranges in master plates. From master plates, compounds were diluted in culture media to obtain test compound solutions for final doses.

After adjustment of the amount of cell medium to 75 μl in each well, 50 μl test compound solution was added. Transiently transfected cells were exposed to compounds for about 24 hours before the luciferase detection assay was performed. For luciferase assays, 100 μl of assay reagent was added manually to each well and plates were left for approximately 20 minutes in order to allow lysis of the cells. After lysis, luciferase activity was measured in a 1420 Multiwell counter, Victor, from Wallach.

Reference Compounds

The TZD pioglitazone was used as reference substance for activation of both human and murine PPARγ. 5,8,11,14-Eicosatetrayonic acid (ETYA) was used as reference substance for human PPARα.

Calculations and Analysis

For calculation of $EC_{50}$ values, a concentration-effect curve was established. Values used were derived from the average of two or three independent measurements (after subtraction of the background average value) and were expressed as the percentage of the maximal activation obtained by the reference compound. Values were plotted against the logarithm of the test compound concentration. $EC_{50}$ values were estimated by linear intercalation between the data points and calculating the concentration required to achieve 50% of the maximal activation obtained by the reference compound.

The compounds of formula I have an $EC_{50}$ of less than 50 µmol/l for PPARα and preferred compounds have an $EC_{50}$ of less than 5 µmol/l. For example the $EC_{50}$s of some of the Examples for human PPAR alpha are:

| Example 3 | 0.499 µmol/l; and |
|---|---|
| Example 5 | 0.048 µmol/l. |

The invention claimed is:

1. A compound of formula I:

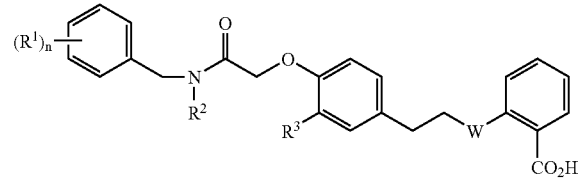

I or a pharmaceutically acceptable salt, or an in vivo cleavable ester thereof, wherein:
n is 0, 1 or 2;
$R^1$ represents halo, a $C_{1-4}$alkyl group which is optionally substituted by one or more fluoro, a $C_{1-4}$alkoxy group which is optionally substituted by one or more fluoro and wherein when n is 2, each $R^1$ may be the same or different;
$R^2$ represents an unbranched $C_{2-7}$alkyl group;
$R^3$ represents H or $OCH_3$; and
W represents O or S.

2. A compound or a pharmaceutically acceptable salt thereof according to claim 1 wherein W is O.

3. A compound or a pharmaceutically acceptable salt thereof according to claim 1 wherein W is S.

4. A compound selected from
2-[2-(4-{2-[ethyl(2-fluorobenzyl)amino]-2-oxoethoxy}phenyl)ethoxy]benzoic acid;
2-[2-(4-{2-[(2,4-difluorobenzyl)(heptyl)amino]-2-oxoethoxy}-3-methoxyphenyl)ethoxy]benzoic acid;
2-[2-(4-{2-[(4-chlorobenzyl)(ethyl)amino]-2-oxoethoxy}phenyl)ethylthio]benzoic acid;
2-[2-(4-{2-[(4-chlorobenzyl)(ethyl)amino]-2-oxoethoxy}phenyl)ethoxy]benzoic acid;
2-[2-(4-{2-[ethyl(4-trifluoromethylbenzyl)amino]-2-oxoethoxy}phenyl)ethoxy]benzoic acid;
2-[2-(4-{2-[ethyl(4-trifluoromethylbenzyl)amino]-2-oxoethoxy}phenyl)ethylthio]benzoic acid;
2-{2-[4-(2-{butyl[2-fluoro-4-(trifluoromethyl)benzyl]amino}-2-oxoethoxy)phenyl]-ethoxy}benzoic acid;
2-[2-(4-{2-[(2,4-difluorobenzyl)(propyl)amino]-2-oxoethoxy}phenyl)ethoxy]benzoic acid;
2-[2-(4-{2-[benzyl(ethyl)amino]-2-oxoethoxy}phenyl)ethoxy]benzoic acid;
2-{[2-(4-{2-[benzyl(ethyl)amino]-2-oxoethoxy}phenyl)ethyl]thio}benzoic acid;
2-[2-(4-{2-[(4-tert-butylbenzyl)(ethyl)amino]-2-oxoethoxy}phenyl)ethoxy]benzoic acid;
2-[2-(4-{2-[ethyl(4-fluorobenzyl)amino]-2-oxoethoxy}phenyl)ethoxy]benzoic acid;
2-{[2-(4-{2-[ethyl(2-fluorobenzyl)amino]-2-oxoethoxy}phenyl)ethyl]thio}benzoic acid;
and
2-{[2-(4-{2-[(2-chlorobenzyl)(ethyl)amino]-2-oxoethoxy}phenyl)ethyl]thio}benzoic acid, or a pharmaceutically acceptable salt thereof.

5. A pharmaceutical formulation comprising a compound according to any one of claims 1 to 4 in admixture with a pharmaceutically acceptable adjuvant, diluent or carrier.

6. A process to prepare a compound of formula I of claim 1 which comprises reacting a compound of formula II:

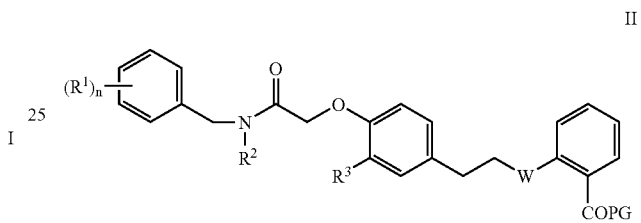

II wherein:
n is 0, 1 or 2;
$R^1$ represents halo, a $C_{1-4}$alkyl group which is optionally substituted by one or more fluoro, a $C_{1-4}$alkoxy group which is optionally substituted by one or more fluoro and wherein when n is 2, each $R^1$ may be the same or different;
$R^2$ represents an unbranched $C_{2-7}$alkyl group;
$R^3$ represents H or $OCH_3$;
W represents O or S; and
PG represents a protecting group for a carboxylic hydroxy group, with a de-protecting agent.

7. A compound of formula II:

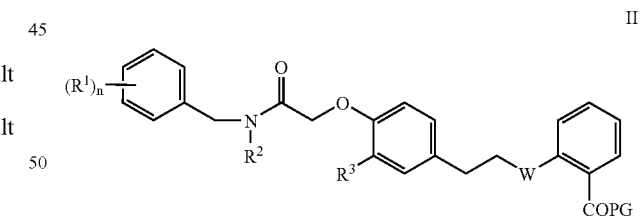

II wherein:
n is 0, 1 or 2;
$R^1$ represents halo, a $C_{1-4}$alkyl group which is optionally substituted by one or more fluoro, a $C_{1-4}$alkoxy group which is optionally substituted by one or more fluoro and wherein when n is 2, each $R^1$ may be the same or different;
$R^2$ represents an unbranched $C_{2-7}$alkyl group;
$R^3$ represents H or $OCH_3$;
W represents O or S; and
PG represents a protecting group for a carboxylic hydroxy group.

* * * * *